| United States Patent [19] | [11] | 4,239,489 |
| Ellman et al. | [45] | Dec. 16, 1980 |

[54] DENTAL THREADED TAPERED POST WITH VENT

[76] Inventors: Alan G. Ellman, 1 Auerbach La., Lawrence, N.Y. 11516; Jon C. Garito, 22 Deering La., East Rockaway, N.Y. 11558

[21] Appl. No.: 9,514

[22] Filed: Feb. 5, 1979

[51] Int. Cl.³ .............................................. A61C 13/08
[52] U.S. Cl. ...................................................... 433/220
[58] Field of Search .................. 32/10 A, 13; 85/1 R, 85/41; 433/220

[56] References Cited

U.S. PATENT DOCUMENTS

| 616,302 | 12/1898 | Evans | 32/13 |
| 622,670 | 4/1899 | Dwight | 32/13 |
| 783,358 | 2/1905 | Bloom | 32/13 |
| 1,091,674 | 3/1914 | Lee | 85/41 |
| 2,242,003 | 5/1941 | Lorenzo | 85/41 |
| 2,705,837 | 4/1955 | Gerlach | 32/13 |

Primary Examiner—Robert Peshock

[57] ABSTRACT

A dental post for build up of a tooth crown is characterized by an outer threaded structure having an upper cylindrical part and a lower tapered part and provided with a longitudinally extending vent. The post can be screwed or cemented into a reamed tooth root canal. The upper threaded part can accommodate a screw-on head.

10 Claims, 10 Drawing Figures

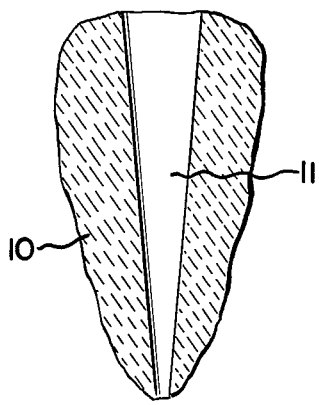
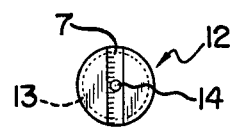
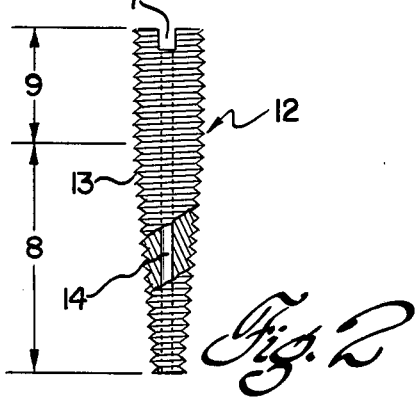
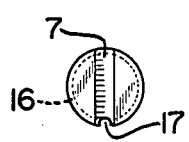
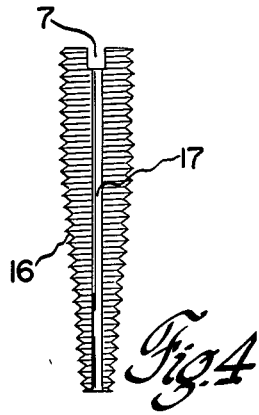
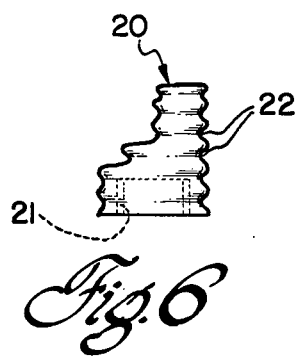
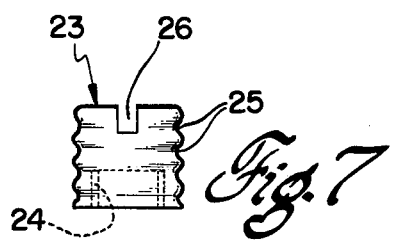
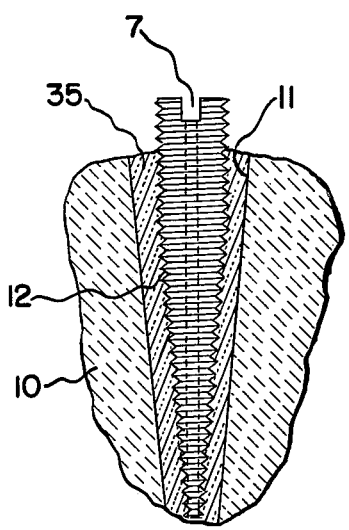
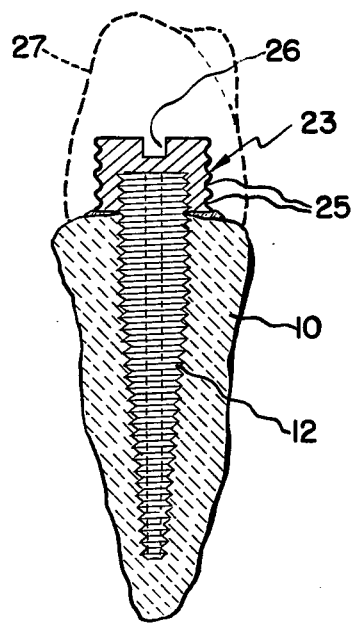

DENTAL THREADED TAPERED POST WITH VENT

This invention relates to a novel dental post construction for mounting in a tooth root canal.

Two basic types of dental posts are currently commercially available to the dental profession for use for crown build up of non-vital teeth. The first is a solid cylindrical or tapered structure which is designed for cementing in the tooth root canal. While it has the advantages of adapting well to the root canal and causing little or no root fracture or crazing, it also exhibits the disadvantages of leaking, of lacking retentive strength, and of possibly causing chemical irritation from the cement. The second type is a solid threaded structure which is designed for screwing into the root canal. While having the advantage of increased retentive strength and less leakage, it also exhibits the disadvantages of being poorly adapted to the root canal, of causing root crazing, and producing excessive air or hydraulic pressure at the bottom of the apical section of the root channel.

The principal object of the invention is a novel dental post free of the disadvantages of the known posts and thus better able to serve the requirements of endodontic root therapy.

In accordance with the invention, the post is constituted over substantially one-half to three-quarters of its length of a tapered lower part adapted to fit substantially the natural contour of the tooth and root canal, and over the remainder of its length of a cylindrical upper part coaxially aligned with the lower part. Further, the post is provided with an outer helical thread over its full length. The threaded lower part allows the post to be screwed or cemented into the root canal, the threads providing added retention in both cases. The threaded upper part serves to support a head element which can be used to screw the post into the canal or when appropriately configured to reinforce the crown. In addition, the post has one or more longitudinal vents to relieve pressure build up at the bottom of the root canal when the post is inserted therein. This pressure build up with the prior art post structures contributed to root crazing and possible root fracture and stress at the apical portion of the root. The vent feature benefits both cemented and non-cemented posts.

These and further objects and advantages of the invention will be better understood from the detailed description that follows of several exemplary embodiments, taken in conjunction with the accompanying drawings wherein:

FIG. 1 is a diagrammatic view of a tooth showing its root canal;

FIGS. 2 and 3 are elevational and end views, respectively, of a first embodiment in accordance with the invention;

FIGS. 4 and 5 are elevational and end views, respectively, of a second embodiment in accordance with the invention;

FIG. 6 is an elevational view of one form of screw-on head for the post of the invention;

FIG. 7 is an elevational view of another form of screw-on head for the post of the invention;

FIG. 8 illustrates the post of FIGS. 2 and 3 screwed into a root canal;

FIG. 9 illustrates the post of FIGS. 2 and 3 cemented in a root canal.

FIG. 10 illustrates the post of FIGS. 2 and 3 containing the screw-on head of FIG. 7 screwed into a root canal.

Referring now to the drawings, FIG. 1 is a diagrammatic view of a typical tooth 10 having a root canal 11. As will be noted, the root canal 11 has a natural tapered shape which becomes smaller as the bottom of the root is approached. The invention is a dental post configured to match the natural tapered shape of the root channel 11 for mounting therein.

FIGS. 2 and 3 illustrate a first embodiment of the invention, comprising an elongated steel post 12 having a fine helical screw thread 13 extending along its entire exterior. In a preferred embodiment, the post is made of stainless steel, titanium, brass, or gold-plated steel to resist corrosion and achieve good bonding to dental amalgams and composite core materials from which the crown will be constituted. The head or wide end of the post is flat and has at the top a slot 7 for accommodating a screw-driver. A hole 14 extends through the center of the entire post, from top to bottom. The hole 14 serves as a vent for air or liquids or cement in the root canal and prevents undesirable build up of pressure in the root canal. The post 12 is divided into a lower tapered part indicated by reference numeral 8 and a cylindrical upper part indicated by reference numeral 9 coaxial with the lower part. The lower part 8 constitutes one-half to three-quarters of the total length of the post, and the upper part 9 constitutes one-half to one-quarter of the total length. Preferably, the lower part 8 is two-thirds and the upper part one-third the overall post length. In a typical embodiment, the post is three-quarters of an inch long with a diameter at the bottom of about 0.035 inches and a diameter at the top of about 0.045 inches. However, this is not meant to be limiting and other dimensions can also be chosen so long as a tapered shape results at the lower part.

In use, the root channel is reamed out with a tapered drill or reamer. Preferably, a self-limiting reamer is used, provided with a stop to limit the reaming depth. If the post is to be screwed into the root canal, the tapered drill has slightly smaller dimensions, eg., 0.001 inches, than the post so that the latter can be screwed into the tooth dentin using the slot 7 for driving purposes, as illustrated in FIG. 8. The upper part of the post is left projecting above the tooth surface. The length of the projecting post part can be adjusted or shortened by cutting the top section with a diamond disc, for example along the plane indicated in FIG. 8 by the dashed line 6.

When the post is to be cemented into the root canal, a tapered reamer is chosen which is slightly oversized compared to the post. In fitting the tapered screw post into the canal there should be a snug fit allowing the post to be moved up and down. As shown in FIG. 9, dental cement 35 can then be used to mount the post 12 in the root canal 11. A suitable cement for this purpose is a cyanoacrylate cement, which has the further advantage of sealing the tooth and preventing leakage. In both cases, the longitudinal vent 14 serves to vent air, liquids or cement in the canal thus enabling the post 12 to be completely seated at the bottom of the channel 11 by eliminating undesired pressure build up. The reamer used for the canal should have a tapered shape corresponding to that of the post lower part.

FIGS. 4 and 5 show a second embodiment similar to the first and comprising a finely-threaded screw 16 with tapered lower part and cylindrical upper part, except that in this embodiment the vent is formed by a groove 17 extending longitudinally along the full side of the post. The groove or flute 17 serves the same venting function as the hole 14 in the first embodiment. If desired, additional grooves 17 may be added along other sides of the post.

After the post 12 has been mounted in the tooth canal, and the upper part adjusted to length, it is now ready to receive the composite build-up or tooth crown. This procedure is suitable for narrow or multi-rooted teeth.

A further feature of the invention is the addition to the upper post part 9 of a screw-on head provided with an exterior configuration to improve retention of the composite material or tooth crown. The addition of the screw-on head provides for excellent adjustment for occlusion by allowing the screw post to be shortened as illustrated in FIG. 8 and then the head top screwed on the post. The screwed-on head can be screwed on and off for adjustment purposes. The exterior of the head can be provided with horizontal grooves or flutes to improve retention of the crown. As an alternative, the exterior can be roughened as by sandblasting. The head can also be trimmed or contoured to conform to desired anatomical form. If necessary, this can be done outside of the mouth. Different shapes of the head can be provided, for example, to accommodate the anterior and posterior of the mouth.

FIG. 6 shows one form of head 20 for anterior mouth use. It can be of the same metal as that of the post. The head 20 comprises a threaded hole 21, whose thread matches that of the upper post part 9. Flutes or grooves 22 are provided on the exterior as described above. FIG. 7 illustrates a head 23 for posterior use. It also includes a threaded hole 24 for mounting on the post part 9, and a fluted exterior 25. It also includes a slot 26 on top for accommodating a screw driver. The screw driver slot 26 is especially useful when using a screwed-in post. After the post height has been adjusted, the head 23 is screwed on, and then the slotted head 26 is used to screw the post into the root canal. It is recommended that cement be added to the post threads as well as the head threaded hole. When the post is screwed in, the head becomes permanently secured or attached to the post by the cement producing a strong retentive connection extending the total length of the canal. The cement also acts as a sealer for the canal, with excess cement and other canal liquids or air being vented up the vent 14 or 17 to the outside or into the threaded hole in the head. Where the post has a center vent, a vertical hole can if desired be provided in the head aligned with and meeting the center vent for additional venting action through the head.

FIG. 10 illustrates the final configuration. The post 12 with screwed-on head 23 is shown screwed into the canal of tooth 10. Reference numeral 27 schematically illustrates in phantom a composite build-up or crown.

As is evident from the above description, the combination of the lower tapered shape and the vent act to reduce stress in the root canal and prevent the build up of excessive air or hydraulic pressure when the threaded post is cemented or screwed into the canal in the course of construction of a crown for the tooth. The screw-on head in different configurations improves occlusion and increases retention of the tooth crown. The combination provides a post construction that is rational, practical, capable of low-cost manufacture, and economical for the efficient production of post-retained restorations.

While our invention has been described in connection with specific embodiments thereof, those skilled in the art will recognize that various modifications are possible within the principles enunciated herein and thus the present invention is not to be limited to the specific embodiments disclosed.

What is claimed is:

1. A dental post for mounting in a tooth root canal, comprising an elongated metal member having on its exterior along substantially its entire length a fine helical thread, said metal member being constituted of a tapered lower part extending along substantially one-half to three-quarters of its full length and coaxial therewith a cylindrical upper part, said metal member having a vent extending along its full length, a head element having an internal threaded hole in threaded engagement with the upper part of said metal member, and means on the head element for receiving screw driving means for screwing the post into the root canal.

2. A dental post for mounting in a tooth root canal, comprising an elongated metal member having on its exterior along substantially its entire length a fine helical thread, said metal member being constituted of a tapered lower part extending along substantially one-half to three-quarters of its full length and coaxial therewith a cylindrical upper part, said metal member having a vent extending along its full length, and a head element having an internal threaded hole in threaded engagement with the upper part of said metal member, in combination with plural head elements each having the same threaded hole but a different outer configuration.

3. A dental post as claimed in claim 2 wherein the vent comprises a hole extending through the center of the elongated metal member.

4. A dental post as claimed in claim 2 wherein the vent comprises a groove extending along the threaded side of the metal member.

5. A dental post as claimed in claim 1 wherein the screw driving means comprises a transverse slot.

6. The method of mounting a dental post having a helically threaded exterior extending over a lower tapered part and an upper cylindrical part in a tooth root canal, comprising the steps of securing the post in the root canal to a depth not substantially exceeding the length of the lower tapered part, trimming off excess portions of the upper cylindrical part, screwing a head onto the remaining cylindrical part, permanently securing the head to the post, and building a tooth restoration over the head.

7. The method of mounting a vented dental post having a helically threaded exterior over a lower tapered part and an upper cylindrical part in a tooth root canal, comprising the steps of fitting the post to the root canal to a depth not substantially exceeding the length of the lower tapered part, screwing a head having screw driving means onto the upper cylindrical part, applying cement to the root canal or the post and screwing the latter into the root canal, excess cement being carried up the vent to the head and securing the latter to the post upon hardening, and building a tooth restoration over the head.

8. A dental post for mounting in a tooth root canal, comprising an elongated metal member having on its exterior along substantially its entire length a fine helical thread, said metal member being constituted of a tapered lower part extending along substantially one-half to three-quarters of its full length and coaxial therewith a cylindrical upper part, said metal member having a vent extending along its full length, and a head element having an internal threaded hole in threaded engagement with the upper part of said metal member, said head element comprising laterally projecting flutes.

9. A dental post as claimed in claim 8 wherein the post is constituted of a non-corrosive metal and has a slotted top.

10. The method of mounting a vented dental post having a helically threaded exterior over a lower tapered part and an upper cylindrical part in a tooth root canal, comprising the steps of fitting the post to the root canal to a depth not substantially exceeding the length of the lower tapered part, applying cement to the root canal or the post and screwing the latter into the root canal to the desired depth leaving the post cylindrical part projecting above the tooth, excees cement, air and moisture being carried up the vent to the exterior, trimming off undesired excess portions of the upper cylindrical part still leaving a portion projecting above the tooth, and building a tooth restoration over the projecting post portion.

* * * * *